(12) United States Patent
Woodard et al.

(10) Patent No.: US 8,388,649 B2
(45) Date of Patent: Mar. 5, 2013

(54) STAGED IMPLANTATION OF VENTRICULAR ASSIST DEVICES

(75) Inventors: John Campbell Woodard, Thornleigh (AU); Geoffrey Douglass Tansley, Mt. Colah (AU)

(73) Assignee: Thoratec Corporation, Pleasanton, CA (US)

( * ) Notice: Subject to any disclaimer, the term of this patent is extended or adjusted under 35 U.S.C. 154(b) by 1100 days.

(21) Appl. No.: 11/713,675

(22) Filed: Mar. 5, 2007

(65) Prior Publication Data
US 2007/0161847 A1 Jul. 12, 2007

Related U.S. Application Data

(62) Division of application No. 10/478,410, filed on Nov. 21, 2003, now abandoned.

(30) Foreign Application Priority Data

May 21, 2001 (AU) .................................... PR5142

(51) Int. Cl.
*A61B 17/12* (2006.01)
(52) U.S. Cl. ........................... 606/213; 606/214; 600/16
(58) Field of Classification Search .......... 606/213–216, 606/200; 600/16
See application file for complete search history.

(56) References Cited

U.S. PATENT DOCUMENTS

| | | | |
|---|---|---|---|
| 4,573,480 A | 3/1986 | Hirschberg | |
| 4,995,857 A | 2/1991 | Arnold | |
| 5,098,370 A | 3/1992 | Rahat et al. | |
| 5,211,546 A | 5/1993 | Isaacson et al. | |
| 5,219,361 A | 6/1993 | Von Recum et al. | |
| 5,289,821 A | 3/1994 | Schwartz | |
| 5,370,509 A | 12/1994 | Golding et al. | |
| 5,470,208 A | 11/1995 | Kletschka | |
| 5,626,562 A | 5/1997 | Castro | |
| 5,695,471 A | 12/1997 | Wampler | |
| 5,755,762 A | 5/1998 | Bush | |
| 5,833,664 A | 11/1998 | Seare, Jr. | |
| 5,840,070 A | 11/1998 | Wampler | |
| 5,879,375 A | 3/1999 | Larson, Jr. et al. | |
| 5,941,813 A | 8/1999 | Sievers et al. | |
| 5,989,215 A | 11/1999 | Delmonte et al. | |
| 6,066,086 A | 5/2000 | Antaki et al. | |
| 6,071,093 A | 6/2000 | Hart | |
| 6,080,133 A | 6/2000 | Wampler | |
| 6,100,618 A | 8/2000 | Schoeb et al. | |
| 6,120,537 A | 9/2000 | Wampler | |
| 6,158,984 A | 12/2000 | Cao et al. | |
| 6,159,232 A * | 12/2000 | Nowakowski ................ 606/213 |
| 6,217,541 B1 | 4/2001 | Yu | |
| 6,227,797 B1 | 5/2001 | Watterson et al. | |
| 6,227,817 B1 | 5/2001 | Paden | |
| 6,228,018 B1 | 5/2001 | Downey et al. | |
| 6,234,772 B1 | 5/2001 | Wampler et al. | |
| 6,234,998 B1 | 5/2001 | Wampler | |

(Continued)

FOREIGN PATENT DOCUMENTS

| | | |
|---|---|---|
| CA | 2237203 | 3/1998 |
| EP | 1 354 606 | 10/2003 |
| JP | 2002-224066 | 8/2002 |
| JP | 2004-278375 | 10/2004 |
| WO | WO 97/29795 | 8/1997 |
| WO | WO-0018469 A1 | 4/2000 |
| WO | WO-0038757 A1 | 7/2000 |
| WO | WO-0059748 A1 | 10/2000 |
| WO | WO 01/05023 | 1/2001 |
| WO | WO 01/12070 | 2/2001 |
| WO | WO 03/015609 | 2/2003 |
| WO | WO 2004/028593 | 4/2004 |

*Primary Examiner* — Rex R Holmes
(74) *Attorney, Agent, or Firm* — Squire Sanders (US) LLP

(57) ABSTRACT

The invention comprises an embolization device for insertably sealing a cannula. The embolization device comprises a sealing cap at a first end and a carrier surface at a second end. The carrier surface is adapted to carry a coagulating material and induces an embolism at a position proximal to the second end and an elongate stem adapted to be inserted within the cannula.

4 Claims, 3 Drawing Sheets

U.S. PATENT DOCUMENTS

| | | |
|---|---|---|
| 6,264,635 B1 | 7/2001 | Wampler et al. |
| 6,368,083 B1 | 4/2002 | Wampler |
| 6,554,851 B1 * | 4/2003 | Palasis et al. ............... 606/213 |
| 6,623,420 B2 | 9/2003 | Reich et al. |
| 6,688,861 B2 | 2/2004 | Wampler |
| 7,048,710 B1 * | 5/2006 | Cragg et al. ............... 604/15 |
| 2001/0009645 A1 | 7/2001 | Noda |
| 2002/0183628 A1 | 12/2002 | Reich et al. |
| 2004/0084398 A1 | 5/2004 | Breitschwerdt et al. |
| 2004/0084399 A1 | 5/2004 | Cook et al. |
| 2004/0234397 A1 | 11/2004 | Wampler |
| 2007/0231135 A1 | 10/2007 | Wampler et al. |
| 2008/0080983 A1 | 4/2008 | Wampler et al. |
| 2008/0085184 A1 | 4/2008 | Wampler et al. |
| 2008/0089779 A1 | 4/2008 | Wampler et al. |
| 2008/0089797 A1 | 4/2008 | Wampler et al. |

* cited by examiner

STAGED IMPLANTATION OF VENTRICULAR ASSIST DEVICES

CROSS REFERENCE

This application is a Divisional of application Ser. No. 10/478,410, filed on Nov. 21, 2003 (abandoned), which claims priority to Australia Patent Application No. PR5142, filed May 21, 2001, the entire contents of which are hereby incorporated by reference.

The present invention relates to systems and devices for the implantation of ventricular assist devices and, more particularly, to such systems and devices suited to a staged regime.

BACKGROUND

Blood pumps are known for the purpose of assisting the pumping function of a heart in a mammal.

In one particular form a class of pumps known as "ventricular assist devices" assist, by pumping, the action of the left ventricle of the heart.

Blood pumps suited for this task include those disclosed in U.S. Pat. No. 6,227,797 (Watterson et al) and U.S. Pat. No. 5,470,208 (Kletschka).

At the present time such pumps are relatively expensive, partly due to current relatively low production runs and partly because of the relatively expensive materials which must be utilized for the task of pumping blood so as to maximize reliability of the pump and minimize the possibility of blood damage.

It has been observed that, in some patients, the "assist" function provided by a ventricular assist device permits the heart to recover function to the point where the ventricular assist device can be removed and the patient's own heart takes over full pumping function.

Unfortunately, to date, no way has been found to predict the likelihood of a temporary assist leading to satisfactory or sufficient recovery of heart pump function.

It is an object of the present invention, in at least preferred embodiments, to provide a cost effective regime for the use of blood pumps and which takes into account the abovementioned problems.

BRIEF DESCRIPTION OF INVENTION

Accordingly, in one broad form of the invention there is provided an embolisation device for insertably sealing a cannula, wherein said embolisation device comprises a sealing cap at a first end, a carrier surface at a second end; wherein the carrier surface is adapted to carry a coagulating material and induces an embolism at a position proximal to said second end and an elongate stem adapted to be inserted within the cannula.

Preferably said embolisation device seals a cannula at a sealing point proximal to a heart of a patient, in use.

Preferably said sealing cap is adapted to be sealingly connected to a corresponding connector of the cannula.

Preferably the elongated stem is of a length so that when the device is entirely inserted within said cannula, the carrier surface is positioned to deliver coagulating material to a sealing point at some point proximal to a heart of a patient, in use.

Preferably said sealing point is sufficiently close to the heart so that there is no requirement to remove the cannula from the body.

Preferably said embolisation device is connected removably and releasably to the cannula, in use.

BRIEF DESCRIPTION OF DRAWINGS

One embodiment of the present invention will now be described with reference to the accompanying drawings wherein.

DETAILED DESCRIPTION OF PREFERRED EMBODIMENT

Figure 1:
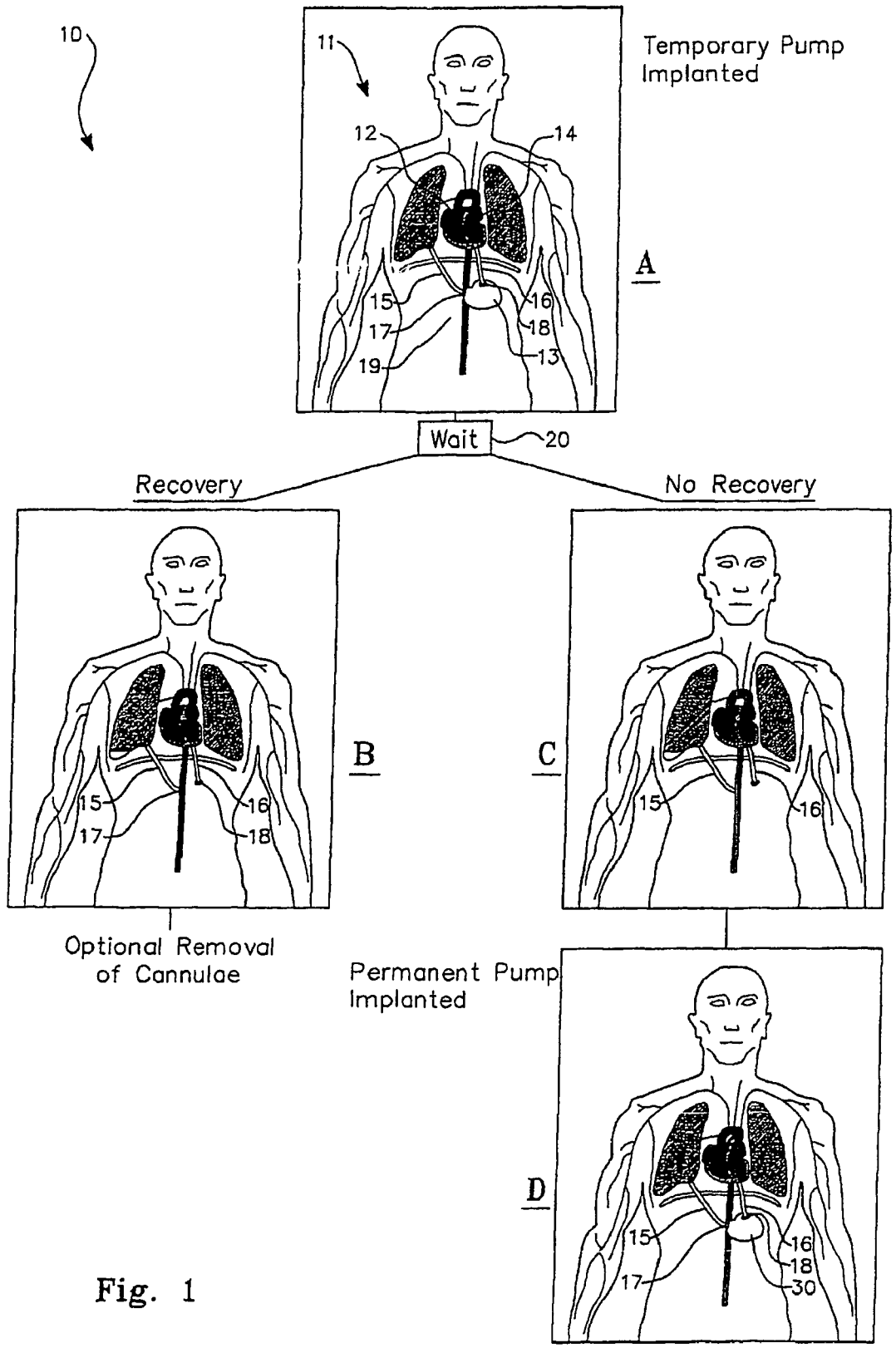
FIG. 1 is a flow diagram illustrating steps in an implantation regime in accordance with a first preferred embodiment of the present invention.

With reference to FIG. 1 comprising sub-diagrams 1A, 1B, 1C and 1D there is illustrated steps in an implantation regime 10 according to a first preferred embodiment of the present invention.

In FIG. 1A a patient 11 having a heart 12 in need of at least an assisted pumping action is fitted with a first ventricular assist device 13 arranged, in this instance, to provide a pumped blood flow "in parallel" across left ventricle 14 of heart 12.

In this instance the fluid connection is effected by first cannula 15 and second cannula 16 as illustrated in FIG. 1.

More particularly first cannula 15 sealingly connects via first connector 17 to ventricular assist device 13 whilst second cannula 16 sealingly connects to ventricular assist device 13 by way of second connector 18.

In this instance the length of cannulae 15, 16 is such as to permit first ventricular assist device 13 to be placed in the abdomen 19 of patient 11.

As will be discussed further below the intention is that first ventricular assist device 13 is to be utilized for a relatively short predetermined period of time, typically up to approximately 3 to 6 months. This predetermined period of time will be sufficient to monitor the function of heart 12 so as to determine whether the assistance provided by first ventricular assist device 13 is sufficient to allow full or substantial recovery of heart 12 to the point where no ventricular assist device is required.

In this event, as shown in FIG. 1B, at the end of the predetermined period of time 20 the first ventricular assist device 13 is removed from the abdomen 19 and first connector 17 and second connector 18 sealed.

Figure 2:
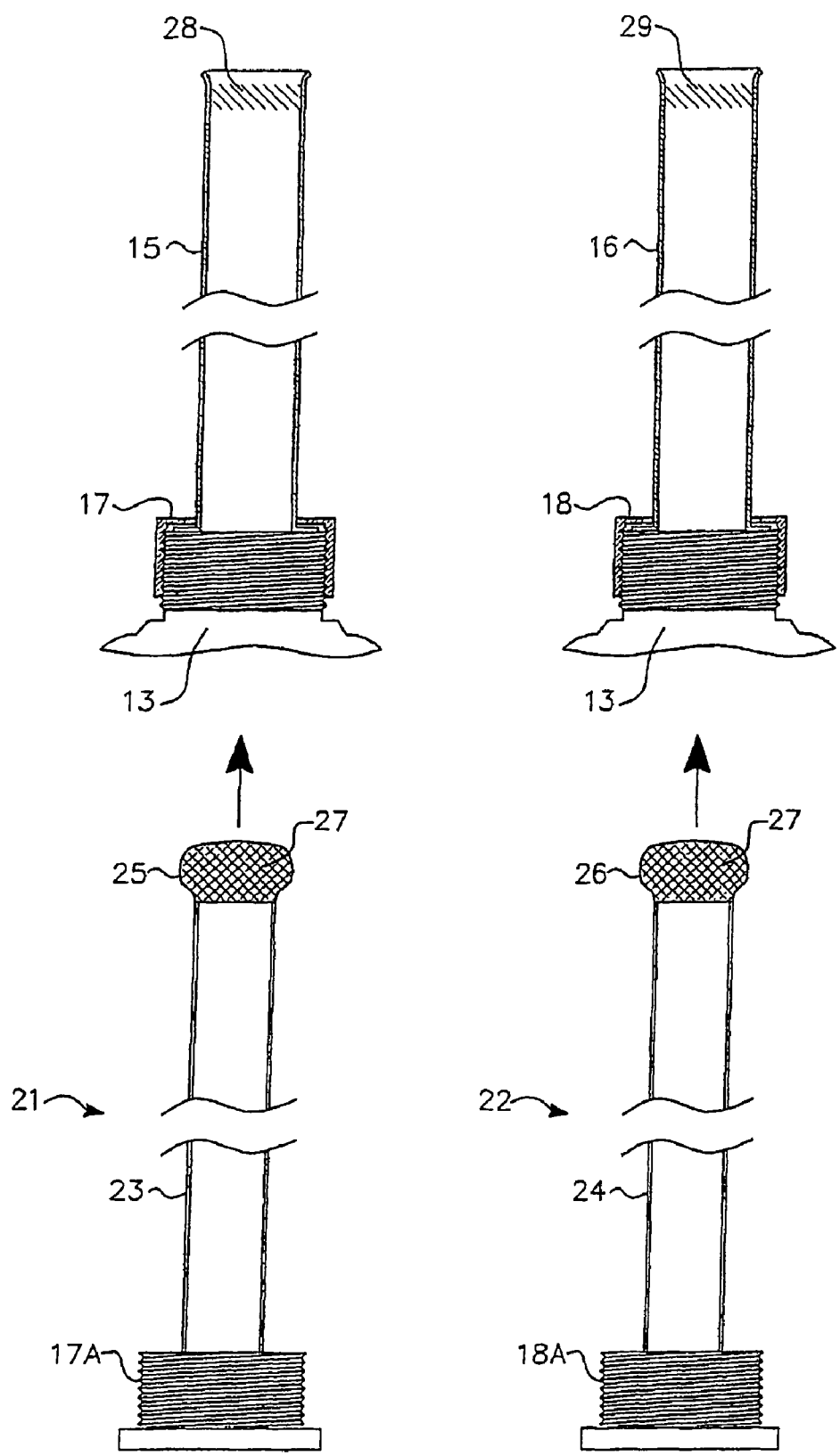
FIG. 2 is a side section view of cannulae and an embolisation tool in accordance with a particular embodiment of the present invention.

In a particularly preferred form, as illustrated in FIG. 2, cannulae 15, 16 are sealed internally at a point sufficiently close to the heart 12 that there is no need to remove cannulae 15, 16 at the time that first ventricular assist device 13 is removed.

Sealing can be effected by use of a first embolisation tool 21 and a second embolisation tool 22 for respective first cannula 15 and second cannula 16.

Each tool 21, 22 comprises an elongate stem 23, 24 respectively having sealing caps 17A, 18A respectively at a first end (refer FIG. 2) and a carrier surface 25, 26 at respective second ends.

The carrier surfaces 25, 26 are adapted to carry a coagulating material 27. The sealing caps 17A, 18A are adapted to be sealingly connected to first connector 17 and second connector 18 respectively upon insertion of the entire length of stems 23, 24 into cannulae 15, 16.

The length of stems 23, 24 is selected so that when tools 21, 22 are entirely inserted within cannulae 15, 16 the carrier surfaces 25, 26 are positioned so as to deliver coagulating material 27 to sealing positions 28, 29 which are sufficiently close to the heart 12 that, upon sealing of cannulae 15, 16 at positions 28, 29 there is no requirement to remove cannulae 15, 16 from the body.

Typically it will be clear within a predetermined period of between one and three months of use of first ventricular assist device 13 as to whether sufficient recovery of heart 12 will be made that the option of removal of first ventricular assist device 13 and appropriate sealing or removal of cannulae 15, 16 can take place as outlined in step B of FIG. 1.

Once the predetermined period 20 has expired and it is judged that heart 12 is unlikely to recover then, as per steps C and D in FIG. 1 first ventricular assist device 13 is removed and immediately replaced with second ventricular assist device 30.

The replacement is performed by disconnecting first connector 31 of first VAD 13 from first connector 17 of first cannula 15 and disconnecting second connector 33 of first VAD 13 from first connector 18 of second cannula 16, withdrawing first ventricular assist device 13 from abdomen 19 and immediately substituting therein second ventricular assist device 30 and then connecting first connector 32 of second ventricular assist device 30 to first cannula 15 and second connector 34 of second ventricular assist device 30 to second cannula 16 by way of respective first connections 17, 18 of cannulae 15, 16.

Ideally, immediately prior to disconnection of first ventricular device 13, cannulae 15,16 are clamped so no air can enter or blood leak out. The clamps are maintained while second ventricular assist device 30 is connected to the same cannulae. The clamps are removed once connection is completed.

Figure 3:
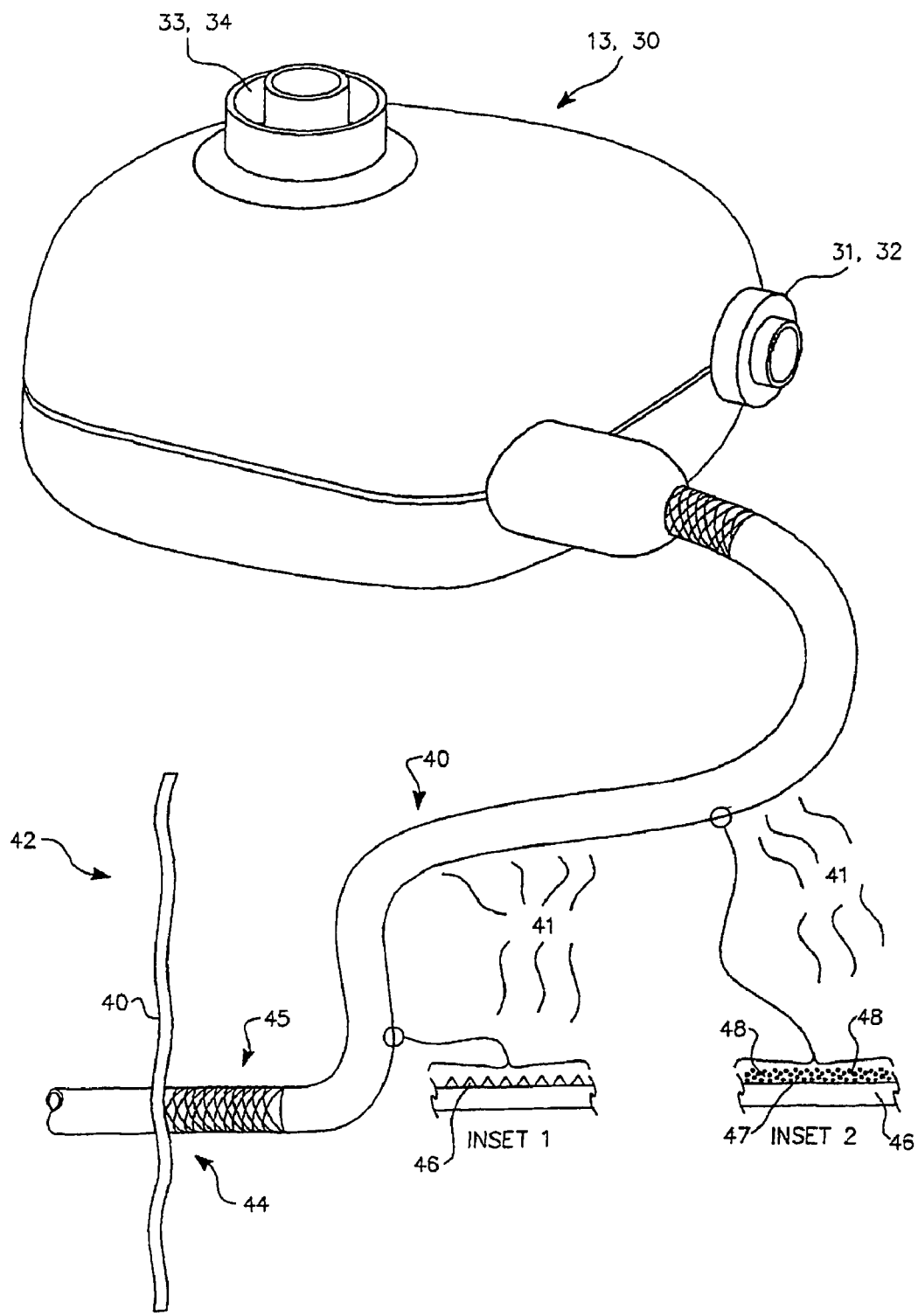
FIG. 3 is a cross-section through a patient's chest and abdomen showing the ventricular assist device in place and the path of the percutaneous lead from the exit site in the skin to the ventricular assist device.

With reference to FIG. 3 there is illustrated an exemplary ventricular assist device 13, 30 having respective first connectors 31, 32 and respective second connectors 33, 34 for the passage of blood through the device.

The ventricular assist device 13, 30 requires power which is conducted through percutaneous lead 40 from outside of the body via exit site 44.

To facilitate the removal of the percutaneous lead 40 which carries electrical energy and control to the ventricular assist device 13 (and subsequently second ventricular assist device 30), the outer surface of the percutaneous lead 40 may be treated so as to prevent the incorporation into surrounding tissue 41 of the percutaneous lead 40. Such surface treatment may extend the entire length of the percutaneous lead 40, or may be terminated just below the surface 43 of the skin 42 so as to allow full incorporation at the exit site 44 and hence a barrier to infection. An example of surface treatment of the percutaneous lead 40 is the use of silicone rubber which naturally resists incorporation. Incorporation at or near the exit site 44 may be achieved through the use of adhesively bonded woven velour 45 or other material or surface treatment which will provide tissue ingrowth as the outermost surface of the percutaneous lead in this region. Alternatively the surface treatment can comprise texturing of surface 46 of lead 40.

As shown in inset 1 in FIG. 1 the texturing of surface 46 of lead 40 can be such that ingrowth of tissue 41 can be only mildly anchored, for example by the use of a pyramid-shaped texture whereby there is little anchoring of tissue to surface 46. Alternatively the texturing can include a labyrinth arrangement such as illustrated in inset 2 of FIG. 3 wherein tissue 41 can follow a labyrinth path through the interstices 48 of labyrinth texture 47.

As previously stated the texture can extend the entire length of lead 40 within the body from the exit site 44 through to device 13, 30. In the alternative the texturing may be at selected and predetermined locations.

The texturing itself can be tailored whereby the degree of tissue ingrowth into the surface 46 is controlled and tailored as a function of displacement along the surface of lead 40.

The surface can be tailored to provide a high degree of ingrowth such as that provided by inset 2 or can be tailored to provide only minimal ingrowth as, for example, provided in inset 1.

It is to be noted that, because of the location of both first ventricular assist device 13 and second ventricular assist device 30 in abdomen 19, permitted by appropriate selection of cannulae 15, 16 it follows that the substitution of second ventricular assist device 30 for first ventricular assist device 13 may take place without patient ventilation or formal heart bypass during the procedure because there is no need to open the chest cavity of patient 11. This arrangement thereby may significantly limit risk to the patient as compared with the situation where general anaesthesia or heart bypass is required.

Second ventricular assist device 30 is intended for long term operation which is to say for many years, ideally extending to beyond the expected lifetime of patient 11.

In particular both first ventricular assist device 13 and second ventricular assist device 30 will, ideally, share the same surgically created pocket in abdomen 19.

Broadly, it will be appreciated that first ventricular assist device 13 is intended for short term use and thereby can have its characteristics selected for short term use whilst second ventricular assist device 30 is intended for long term use and therefore can have its characteristics selected for long term use.

By way of example first ventricular assist device 13 can take the form of almost any blood pump including those disclosed in U.S. Pat. No. 6,227,797 (Watterson et al) and U.S. Pat. No. 5,470,208 (Kletschka) provided only that the blood pump is sized to fit in the pocket created in abdomen 19. In particular the first ventricular assist device 13 may comprise an axial or centrifugal pump, or sac-type device. Its impeller may be suspended in any number of ways including mechanically, magnetically and hydrodynamically or by a combination of these. In the case of a sac-type device urging of the blood through the device may be caused by the reciprocating action of a pusher-plate or similar mechanism in a sac-type device.

Its components can be made using mass production techniques and utilising less expensive materials than for the long life second ventricular assist device.

In particular the components comprising the pump casing and internal surfaces and rotating parts can be made from plastic materials including polymeric materials.

Coatings (such coatings not necessarily having a significantly long life) can be applied so as to increase blood compatibility. It is noted that some plastic materials such as covalently bonded heparin are particularly suited to receive and support such coatings. The Carmeda process can be utilized to perform the covalent bonding of Heparin. In addition or alternatively the coating may constitute a slow-release antibiotic.

In a further particular form the first ventricular assist device 13 adapted for short term use need not be hermetically sealed. Instead it may comprise one or more components in respect of which slow permeation of body fluids is acceptable. Examples of slow permeation materials which may be suitable include polypropylene, epoxy or nylon.

Conversely, second ventricular assist device 30 is constructed for long term (which is to say much greater than 3 months and typically, of the order of many years) reliable operation and can embody, for example, the principles of rotor support described in U.S. Pat. No. 6,227,797 (Watterson et al) and U.S. Pat. No. 5,470,208 (Kletschka). In this instance, suitable materials from which to construct the pump casing and/or the pump rotor for reliable, long term operation include hermetically welded titanium alloy.

The above describes only some embodiments of the present invention and modifications, obvious to those skilled in the art can be made thereto without departing from the scope and spirit of the present invention.

The invention claimed is:

1. An embolisation device for sealing a cannula, comprising:
   an elongated stem having a first end and a second end;
   a sealing cap at the first end, configured to sealingly connect to the cannula; and
   a carrier surface at the second end including a coagulating material on the second end for inducing an embolisation at a sealing position of the cannula;
   wherein the coagulating material is placed at the sealing position of the cannula when the stem is inserted into the cannula; and
   wherein the cannula and stem are configured to remain within a patient.

2. The embolisation device of claim 1 wherein the embolisation device is configured for sealing the cannula at a sealing point adjacent to a heart of the patient, during use.

3. The embolisation device of claim 1 wherein the sealing cap has a threading adapted for engaging a complimentary threading disposed on the cannula.

4. The embolisation device of claim 1, wherein the embolisation device is configured for sealing the cannula when the entire length of the stem is inserted into the cannula.

* * * * *